United States Patent
Brazdil

(10) Patent No.: US 6,887,825 B2
(45) Date of Patent: May 3, 2005

(54) METHOD FOR THE PREPARATION OF VANADIUM-ANTIMONY-OXIDE BASED OXIDATION AND AMMOXIDATION CATALYSTS USING NON-AQUEOUS MEDIA

(75) Inventor: James F. Brazdil, Glen Ellyn, IL (US)

(73) Assignee: The Standard Oil Company, Warrenville, IL (US)

( * ) Notice: Subject to any disclaimer, the term of this patent is extended or adjusted under 35 U.S.C. 154(b) by 0 days.

(21) Appl. No.: 10/306,383

(22) Filed: Nov. 27, 2002

(65) Prior Publication Data
US 2004/0102319 A1 May 27, 2004

(51) Int. Cl.⁷ .......................... B01J 23/22; B01J 23/16
(52) U.S. Cl. ................ 502/353; 502/354; 502/311; 502/312; 502/319; 502/325; 502/340; 502/338; 502/349; 502/350; 502/352; 502/355
(58) Field of Search ................ 502/353, 354, 502/311, 312, 319, 325, 340, 338, 349, 350, 352, 355

(56) References Cited

U.S. PATENT DOCUMENTS

| | | | |
|---|---|---|---|
| 3,681,421 A | 8/1972 | Barclay et al. | 160/465.3 |
| 3,860,534 A | 1/1975 | Harris et al. | 252/461 |
| 4,336,205 A | 6/1982 | Onishi et al. | 260/465 |
| 4,746,641 A | 5/1988 | Guttmann et al. | 502/202 |
| 4,784,979 A | 11/1988 | Toft et al. | 502/8 |
| 4,788,317 A | 11/1988 | Guttmann et al. | 558/319 |
| 4,879,264 A | 11/1989 | Toft et al. | 502/8 |
| 5,008,427 A | 4/1991 | Brazdil, Jr. et al. | 558/319 |
| 5,094,989 A | 3/1992 | Lynch et al. | 502/202 |
| 5,214,016 A | 5/1993 | Brazdil et al. | 502/202 |
| 5,258,543 A | 11/1993 | Suresh et al. | 558/325 |
| 5,332,855 A | 7/1994 | Blanchard et al. | 558/319 |
| 5,432,141 A | 7/1995 | Brazdil, Jr. et al. | 502/311 |
| 5,498,588 A | 3/1996 | Brazdil et al. | 502/353 |
| 5,663,392 A | 9/1997 | Albonetti et al. | 556/28 |
| 5,675,057 A | 10/1997 | Bremer et al. | 558/319 |
| 5,686,381 A | 11/1997 | Albonetti et al. | 502/352 |
| 5,696,047 A | 12/1997 | Bremer et al. | 502/209 |
| 5,821,192 A | 10/1998 | Seely et al. | 502/353 |
| 5,866,502 A | 2/1999 | Cirjak et al. | 502/353 |
| 5,994,259 A | 11/1999 | Brazdil, Jr. et al. | 502/300 |
| 6,083,869 A | 7/2000 | Albonetti et al. | 502/325 |
| 6,087,524 A | 7/2000 | Brazdil, Jr. et al. | 558/320 |
| 6,156,920 A | 12/2000 | Brazdil, Jr. et al. | 558/319 |
| 6,166,241 A * | 12/2000 | Kayou et al. | 558/318 |
| 6,200,926 B1 | 3/2001 | Blanchard et al. | 502/352 |
| 6,514,902 B1 * | 2/2003 | Inoue et al. | 502/305 |
| 6,589,907 B2 * | 7/2003 | Chaturvedi et al. | 502/311 |
| 6,656,873 B2 * | 12/2003 | Chaturvedi et al. | 502/312 |

FOREIGN PATENT DOCUMENTS

| | | | |
|---|---|---|---|
| GB | 1034914 | | 7/1966 |
| WO | WO 00/12209 | * | 3/2000 |

* cited by examiner

Primary Examiner—Christina Johnson
(74) Attorney, Agent, or Firm—David P. Yusko

(57) ABSTRACT

Vanadium antimony oxide catalysts useful for the selective oxidation and ammoxidation of paraffins, olefins, and aromatic compounds are manufactured in a process comprising (i) forming a catalyst precursor slurry comprising a vanadium containing compound and an antimony containing compound in a liquid solvent medium which comprises an organic solvent, and (ii) recovering a vanadium antimony oxide from the slurry by drying the slurry in order to remove water and organic solvent.

5 Claims, No Drawings

Method for the Preparation of Vanadium-Antimony-Oxide Based Oxidation and Ammoxidation Catalysts Using Non-Aqueous Media

BACKGROUND OF THE INVENTION

1. Field of the Invention

This invention relates to vanadium antimony oxide catalysts for the selective oxidation and ammoxidation of paraffins, olefins, and aromatic compounds. More specifically, the invention relates to a slurry preparation of vanadium antimony oxide based catalysts in a liquid solvent medium comprising an organic solvent.

2. Description of the Prior Art

Commercial processes for the production of acrylonitrile employ propylene as a feedstock. However, because of the price differential between propylene and propane, an economic incentive exists for the development of a commercial process for the ammoxidation of propane to acrylonitrile. The development of such a process depends upon a viable catalyst useful for the conversion of propane to acrylonitrile.

Catalyst comprising the oxides of vanadium, antimony and optional promoter elements (referred to herein as vanadium antimony oxide catalysts) useful in the ammoxidation of propane to acrylonitrile along with various methods of making such catalysts are taught in the following U.S. Pat. Nos. 5,994,259; 5,866,502; 5,498,588; 5,332,855; 5,258,543; 5,214,016; 5,008,427; 4,788,317; 4,784,979; 4,746,641; 3,860,534; and 3,681,421. The preparation of vanadium antimony type catalysts disclosed in these patents all react a slurry of the vanadium and antimony source compounds in a wholly aqueous medium. U.S. Pat. No. 6,083,869, vanadium and antimony source compounds are dissolved in a saturated alcohol or a mixture of saturated alcohol and water, and then contacted with an ammonium salt in order to precipitate the vanadium antimony oxide.

SUMMARY OF THE INVENTION

Then invention relates to vanadium antimony oxide catalysts having lower particle densities. Specifically, the present invention is directed the process for making such catalyst wherein the vanadium antimony oxide catalyst comprises vanadium, antimony, at least one of tin, titanium, iron, chromium and gallium, and optionally at least one element selected from the group consisting of lithium, magnesium, sodium, calcium, strontium, barium, cobalt, nickel, zinc, germanium, niobium, zirconium, molybdenum, tungsten, copper, tellurium, tantalum, selenium, bismuth, cerium, indium, arsenic, boron, aluminum, and manganese, wherein the relative ratios of these elements are represented by the following general formula:

$V_1Sb_mA_aD_dO_x$ wherein A is at least one of Ti, Sn, Fe, Cr, and Ga.

D when present is at least one of Li, Mg, Ca, Sr, Ba, Co, Ni, Zn, Ge, Nb,

Zr, Mo, W, Cu, Te, Ta, Se, Bi, Ce, In, As, B, Al, and Mn, m is between about 0.5 to about 10 a is between about 0 to about 10 d is 0 to about 10 and x is determined by the oxidation state of the cations present, and wherein the process comprises (i) forming a catalyst precursor slurry comprising a vanadium containing compound and an antimony containing compound in a liquid solvent medium which comprises an organic solvent, and (ii) recovering a vanadium antimony oxide from the slurry by drying the slurry in order to remove water and organic solvent.

Further embodiments of present invention are directed to vanadium antimony oxide catalyst produced by the process described above as well as a process for the manufacture of acrylonitrile from a hydrocarbon selected from the group consisting of propylene, propane and mixtures thereof comprising reacting the hydrocarbon with ammonia and oxygen in the presence of such vanadium antimony oxide catalyst.

DETAILED DESCRIPTION OF THE INVENTION

The instant invention relates to vanadium antimony oxide catalysts prepared in a process utilizing a liquid solvent medium which comprises an organic solvent. Prior art slurry preparation methods in a wholly aqueous medium typically produce catalysts having particle densities greater than 1 g/cm$^3$. The method of the instant invention produces a vanadium antimony oxide based catalysts having particle densities of approximately 1 g/cm$^3$. Among the benefits derived from the manufacture of a vanadium-antimony-oxide based catalyst having lower particle density than catalysts prepared by prior art wholly aqueous preparation methods are:

(1) reducing the size (and therefor the capital cost) of a commercial vanadium antimony oxide catalyst charge for reactors in a process for the ammoxidation of propane to acrylonitrile, (2) a vanadium antimony oxide catalyst particle density more suited for operation in commercial fluid-bed reactors, and (3) since a 1 g/cm$^3$ particle density is similar to the particle densities of commercial catalysts used in the ammoxidation of propylene to acrylonitrile, the vanadium antimony oxide catalysts of the instant invention provides a catalyst that is operationally suitable to retrofit an existing propylene ammoxidation reactor for other applications, for example, the ammoxidation of propane to acrylonitrile.

The vanadium antimony catalysts prepared as described herein also exhibit enhanced activity and productivity to useful products compared to catalysts produced by prior art wholly aqueous preparation methods.

Catalyst Composition

The vanadium antimony oxide catalysts described herein comprise vanadium, antimony, at least one of tin, titanium, iron, chromium and gallium, and optionally at least one element selected from the group consisting of lithium, magnesium, sodium, calcium, strontium, barium, cobalt, nickel, zinc, germanium, niobium, zirconium, molybdenum, tungsten, copper, tellurium, tantalum, selenium, bismuth, cerium, indium, arsenic, boron, aluminum, and manganese, wherein the relative ratios of these elements are represented by the following general formula:

$V_1Sb_mA_aD_dO_x$ wherein A is at least one of Ti, Sn, Fe, Cr, and Ga.

D when present is at least one of Li, Mg, Ca, Sr, Ba, Co, Ni, Zn, Ge, Nb,

Zr, Mo, W, Cu, Te, Ta, Se, Bi, Ce, In, As, B, Al, and Mn, $0.5 \leq m \leq 10$, $0 < a \leq 10$, $0 \leq d \leq 10$, and x is determined by the oxidation state of the cations present.

A preferred catalyst formulation, when applied to a process of manufacturing acrylonitrile or methacrylonitrile by catalytic reaction in the vapor phase of a paraffin selected from propane and isobutane with molecular oxygen and ammonia by catalytic contact of the reactants in a reaction zone, comprises vanadium, antimony, iron, at least one of tin, titanium, chromium and gallium, and at least one other promoter element selected from the group consisting of lithium, magnesium, sodium, calcium, strontium, barium, cobalt, chromium, gallium, nickel, zinc, germanium, zirconium, tantalum, bismuth, cerium, indium, boron, aluminum, and manganese, optionally one or more of molybdenum, tungsten and niobium, and optionally one or more of arsenic, tellurium and selenium, wherein the relative proportions of these elements are represented by the following formula:

$$V_1Sb_bA_cFe_dD_eQ_fR_gO_x$$

where

A is at least one of Ti, Sn, Cr, and Ga

D is at least one of Li, Mg, Ca, Sr, Ba, Co, Ni, Zn, Ge, Zr, Cu, Ta, Bi,

Ce, In, B, Al and Mn

Q is selected from the group consisting of Mo, W, Nb,

R is selected from the group consisting of As, Te, Se, and $0.8 \leq b \leq 4$, $0.01 \leq c \leq 2$, $0.01 \leq d \leq 2$, $0 \leq e \leq 2$, $0 \leq f < 0.01$ and more preferably $0 < f < 0.0045$, $0 \leq g < 0.1$, and x is determined by the oxidation state of the cations present.

In the above-described catalysts preferably "A" is both Sn and Ti. Also a preferred catalyst composition is when Q is Mo and R is As.

The above-described catalysts may be unsupported or supported on any suitable carrier. Examples of suitable carriers are silica, alumina, silica alumina, zirconia and the like.

Representative catalyst formulations made by the process of the instant invention include:

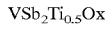

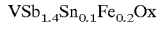

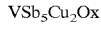

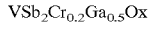

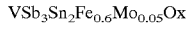

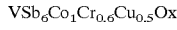

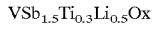

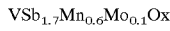

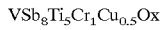

Catalyst Preparation

In the practice of the instant invention, the production of the vanadium antimony oxide based catalysts described herein begins with the preparation of a catalyst precursor dispersion, solution, sol, or slurry comprising vanadium, antimony and optionally other promoter elements, referred to herein as the "catalyst precursor slurry". The slurry is prepared using a liquid solvent medium which comprises an organic solvent. The slurry is then dried in order to remove the water and the solvent and to yield the catalyst precursor. The catalyst precursor is then calcined to yield the finished catalyst.

The hallmark of the instant invention is the use of a liquid solvent medium which comprises an organic solvent, in whole or in part, in the preparation of catalyst precursor slurry. The liquid solvent medium consists of up to 100 wt % of an organic solvent. Preferred is 10 to 100 wt % of an organic solvent, more preferred is 50 to 100 wt %, and most preferred is 80 to 100 wt %. The organic solvent can be added at any time in the catalyst preparation prior to the drying of the catalyst precursor slurry to form the catalyst precursor. The organic solvent may comprise any organic compound or mixtures of organic compounds that is a liquid under the conditions used to prepare the vanadium-antimony-oxide based catalyst. Examples of suitable organic solvents are hydrocarbons, or functionalized organic compounds such as alcohols, nitriles, carboxylic acids, amines, and sulfides. Also suitable are organic compounds containing any combination of chemical functionalities. In general the non-aqueous solvent medium replaces the wholly aqueous mediums employed in most prior art vanadium antimony oxide catalyst preparations.

The general method used to prepare the catalyst, or more specifically the catalyst precursor slurry, is not critical. This vanadium antimony oxide catalyst precursor slurry can be prepared by any method known in the art. Source compound for the vanadium, antimony and promoter elements are as described below.

A particularly effective method of preparation of the catalyst precursor slurry is is disclosed in U.S. Pat. No. 5,866,502. This method comprises heating an aqueous mixture comprising water soluble vanadates (e.g. $VO_4^{-3}$, $VO_3^{-1}$, $V_2O_5$) and $Sb_2O_3$ and, optionally, at least one compound comprising a promoter element to a temperature between 110° C. and 250° C. under autogenous pressure with agitation for a time sufficient to allow at least the slightly water soluble vanadates and $Sb_2O_3$ to react to form the catalyst precursor slurry.

The hydrothermal reaction of the metal oxides in the aqueous solution is continued for a time period sufficient for the metal oxides to suitably react to form the catalyst precursor. The required reaction time is ultimately determined by the catalytic and physical properties of the final material obtained after calcination. Typically, the reaction is continued for between 0.5 to 100 hrs, preferably from 1 to 50 hrs, especially preferred being 1 to 10 hrs. It has been observed that shorter reaction times are required as one increases the temperature employed during the catalyst precursor formation.

An alternative method of preparation of the catalyst precursor slurry is the so-called "peroxide method" disclosed in U.S. Pat. Nos. 4,784,979 and 4,879,264. Specifically according to U.S. Pat. No. 4,784,979, the catalyst precursor slurry is prepared by first preparing a monoperoxovanadium ion, $VO(O_2)^+$, by reacting a vanadium compound with an aqueous hydrogen peroxide ($H_2O_2$) solution, and then reacting the monoperoxovanadium ion, $VO(O_2)^+$, while in aqueous solution, with an antimony compound which contains Sb having a valence of 3, thereby reducing the average valence of the vanadium to less than 5 and oxidizing antimony to a valence state of 5. At least a portion of the $Sb^{+3}$ is so reduced, not necessarily all.

The vanadium source (i.e. the vanadium compound or vanadium containing compound, as used herein) can be an inorganic or an organic compound of vanadium, but is usually an inorganic compound. The vanadium in the compound can have any initial valence. A partial list of such compounds includes any oxide of vanadium, such as $V_2O_5$, $V_7O_{13}$, VO, $VO_2$, $V_2O_3$, $V_3O_7$, etc.; any vanadium oxyhalide such as $VOCl_3$, $VOCl_2$, $(VO_2)Cl$, VOCl, VOBr, $VOBr_2$, $VOBr_3$; any vanadium halide such as $VF_3$, $VBr_3$, $VCl_2$, $VCl_3$, $VCl_4$, $VF_5$; vanadyl sulfate; meta-vanadic acid; pyro-vanadic acid.

For the peroxide method, the vanadium compound usually used in the reaction with $H_2O_2$ is one of the oxides. Because of availability and cost, $V_2O_5$ is often the compound that is chosen to react with the hydrogen peroxide.

The antimony source (i.e. the antimony compound or antimony containing compound, as used herein) can be an organic or an inorganic compound of antimony. A partial list of such compounds includes any of the following types of compounds containing antimony having a valence of 3: any such antimony oxide such as $Sb_2O_3$ and $Sb_2O_4$; SbOCl; any such antimony halide such as $SbBr_3$, $SbCl_3$, $SbF_3$ and $SbI_3$. The preferred antimony source in these preparations is $Sb_2O_3$.

After the vanadium and antimony reaction has taken place, compounds comprising promoter elements may be added. These includes compounds of elements such as Ti, Sn, Fe, Cu, Mg, Mo, As, Li, Ca, Sr, Ba, Co, Ni, Zn, Ge, Nb, Zr, W, Te, Ta, Se, Bi, Ce, In, B, and Mn. Examples of sources of the metal promoters include nitrates, acetates, hydroxides, oxides, ammonium ion complexes, and carbonyls. A preferred promoter is iron derived from an iron containing compound (e.g. $Fe_2O_3$) having a BET surface area of greater than about 120 $m^2$/gram. For iron promoted catalysts, the atomic ratio of iron to vanadium is preferably greater than 0.2. For the peroxide prep described above, compounds of some elements such as Ti that form peroxo compounds can also be added before or with the addition of the $H_2O_2$, but are usually most conveniently added after the vanadium and antimony compounds have reacted. Alternatively, promoter elements may be added in sol form. Alternatively, promoter elements can be added prior to the reaction of the vanadium and antimony reaction as described in U.S. Pat. No. 5,866,502 or promoter elements can be added by impregnation after drying the catalyst precursor slurry to remove water. The addition of promoter elements to the vanadium antimony oxide catalyst precursor slurry or dried catalyst precursor can be achieved by known methods in the art such as ion-exchange, solvo thermal treatment, and impregnation.

An additional alternative is to add promoter elements in sol form. For example, U.S. Pat. No. 6,087,524 discloses the preparation of tin promoted vanadium antimony oxide catalysts using tin sols (made from $SnO_2 \cdot nH_2O$) wherein the tin sol was dispersed in a quaternary ammonium hydroxide. Additionally, a quaternary ammonium hydroxide (e.g. tetramethyl ammonium hydroxide or tetraethyl ammonium hydroxide can be added to the catalyst slurry by itself in order to improve attrition resistance of the final catalyst. The quaternary ammonium hydroxide is added such that the molar ratio of added QAH per gram of finished catalyst is between about 0.001 and about 10, preferably between about 0.005 and about 0.5.

The catalyst can be supported on any suitable carrier. Examples of such carriers are silica, alumina, silica-alumina, and the like. A particularly attrition resistant form of the catalyst contains silica, added as silica sol. Various types of silica sol, with particle sizes of about 5 to about 100 nanometers, can be used. The silica sol may be added to the catalyst precursor slurry at any time prior to drying the catalyst precursor slurry to form the catalyst precursor. Usually, these catalytic grade silica sols have low alkali metal content, and are stabilized by ammonia. Ion exchange with resins in acid or ammonium forms can also be used to remove excess alkali or alkaline earth ions from the silica.

The vanadium antimony catalyst described herein is recovered from the catalyst precursor slurry by drying. After making the catalyst precursor slurry as described above the precursor slurry is dried to remove water and solvent to yield a catalyst precursor which is then calcined to produce the finished catalyst. Optionally, the catalyst precursor slurry may first be concentrated by heating the catalyst precursor slurry in order to evaporate residual quantities of water and/or solvent. These heat treatments can be conducted as separate operations in multiple pieces of equipment or they can be conducted in single piece of equipment wherein the temperature is increased stepwise or continuously over time. In the preparation of a fixed bed catalyst, the catalyst precursor slurry is typically dried by heating at an elevated temperature and then shaped (e.g. extruded, pellitized, etc.) to the desired fixed bed catalyst size and configuration. In the preparation of fluid bed catalysts, the catalyst precursor slurry is typically spray dried to yield microspheroidal catalyst particles having particle diameters in the range from 10 to 200 microns. Unlike U.S. Pat. No. 6,083,869, the promoted vanadium antimony oxide formed during the preparation of the catalyst is not contacted with an ammonium salt to yield a precipitate which is then recovered by filtration.

After the catalyst is dried and shaped into its fixed or fluid bed form, the catalyst is subjected to a high temperature heat treatment or calcination in air or an oxygen enriched environment (i.e. a gaseous environment or atmosphere having a greater oxygen ($O_2$) content than air). The high temperature heat treatment or calcination is conducted at a temperature of at least 600° C., preferably above 750° C. For vanadium antimony oxide catalysts used for the ammoxidation of propane a high temperature heat treatment or calcination at a temperature of at least 780° C. is preferred. The high temperature heat treatment or calcination temperatures can be as high as 1200° C. Preferably the high temperature heat treatment or calcination is conducted at a temperature in the range of about 790° C. to about 1050° C.

Optionally, as disclosed in U.S. Pat. Nos. 5,675,057 and 5,696,047, the catalyst may be further heat treated at an effective temperature that is at least 500° C. and at least 50° C. below said high temperature heat treatment calcination temperature.

The calcining step described above activates the catalyst to a significant degree, optionally the catalyst may be contacted with an alcohol (hydroxy compound) to further activate the catalyst. The catalyst may optionally be washed at any one or more points in the procedure using the methods disclosed in U.S. Pat. Nos. 3,860,534 and/or 5,094,989. Specifically, the catalyst can be washed after calcination by contacting said calcined catalyst with a hydroxy compound in liquid form (usually having no carbon-to-carbon unsaturation) selected from (1) cyclohexanol, (2) cyclopentanol, (3) a monohydroxy, acyclic hydrocarbon having 1–8 C atoms, usually 1–10 C atoms, and (4) a dihydroxy, acyclic hydrocarbon having 2–4 carbon atoms, and separating as a liquid said compound from said catalyst insofar as it is present beyond the amount wetting said catalyst, and thereafter drying said catalyst. Especially useful hydroxy compounds are the monohydroxy, acyclic hydrocarbons having 1 to 8 carbon atoms, and the dihydroxy, acyclic hydrocarbons having 2 to 4 carbon atoms. Most useful are the monohydroxy, acyclic hydrocarbons having 1 to 4 carbon atoms, especially isobutanol.

Processes

In another aspect of the present invention, there is provided a process for making an $\alpha,\beta$ unsaturated mononitrile selected from acrylonitrile and methacrylonitrile, by catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to $NH_3$ in the range of 2.5 to 16 and a mole ratio of said paraffin to $O_2$ in the range from 1 to 10, said catalyst having an empirical composition described above, said catalyst having been made by a method described above. The reaction temperature range can vary from 350° C. to 700° C. but is usually between 430° C. and 520° C. The average contact time can be from 0.01 to 10 seconds but is usually between 0.02 and 10 seconds and more preferably between 0.1 to 5 seconds. The pressure in the reaction zone is usually no more than 75 psia, but is preferably no more than 50 psia.

The catalyst may also be used in the ammoxidation of methylpyridine and mxylene to cyanopyridine and isophthalonitrile or the oxidation of o-xylene to phthalic anhydride. The mole ratios of ammonia to methylpyridine and $O_2$ to methylpyridine are 1 to 5 and 1 to 10, respectively. The mole ratios of ammonia to m-xylene and $O_2$ to m-xylene are 1 to 5 and 1 to 10, respectively. In the phthalic anhydride reaction, the ratio of $O_2$ to o-xylene may range from 1 to 10.

The catalyst prepared by the process of the present invention may also be utilized in the ammoxidation of propylene or isobutene with ammonia and oxygen to produce acrylonitrile or methacrylonitrile. The mole ratio of ammonia to olefin may range from 1 to 5 and the mole ratio of $O_2$ to olefin may range from 1 to 10 in this reaction under conventional temperatures and conditions well known in the art.

The catalyst and processes described herein may be employed in any suitable reactor including fixed-bed, fluid-bed, and transport-bed reactors.

Specific Embodiments

For purposes of illustration only, the following examples are set forth to describe the process of the present invention.
Catalyst Preparation

EXAMPLE 1

A catalyst having the composition $VSb_{1.6}Fe_{0.6}Mo_{0.0022}O_x$ was prepared by adding 9.10 g of $V_2O_5$ along with 30 g of 30 wt % $H_2O_2$ (in water) to 1000 ml of acetonitrile. Six additional aliquots of 30 g of 30 wt % $H_2O_2$ (in water) were added over a period of 1.5 hours whereupon the mixture had the appearance of a dark green sol. 23.32 g of $Sb_2O_3$ were added and the mixture was heated to 70° C. with stirring for about 5 hours. 4.79 g of $Fe_2O_3$ powder were added and the mixture was heated to 70° C. with stirring for an additional 5 hours. The resulting mixture was cooled to room temperature and the liquid was removed from the mixture by decanting. The solid was heated at 120° C. then at 325° C. for 3 hours and 650° C. for 2 hours. The solid was ground and sieved and the 20 to 35 mesh particle size collected. These were then heat treated at 820° C. for 3 hours, cooled to room temperature then washed with isobutanol and dried at 120° C. 2.93 g of the washed catalyst was treated with an aqueous solution of ammonium heptamolybdate to give a Mo/V ratio for the catalyst of 0.002/1. The treated catalyst was dried at 120° C. then heat treated at 325° C. for 3 hours and then at 500° C. for 3 hours.

COMPARATIVE EXAMPLE A

A catalyst having the composition $VSb_{1.6}Sn_{0.05}Ti_{0.5}Fe_{0.45}Mo_{0.0025}O_x$ was prepared by using the prior art peroxide method disclosed in U.S. Pat. Nos. 4,784,979 and 4,879,264. Essentially this preparation was similar to the preparation of Example 1, except that water and tetramethyl ammonium hydroxide were the only solvents used to prepare the catalyst.
Catalyst Testing The catalysts prepared above were tested for the ammoxidation of propane using a fixed-bed micro-reactor made of 0.25 inch O.D. titanium tubing immersed in a temperature controlled molten salt bath. The molar ratios of the feed compositions, reaction temperatures and contact times for the tests are listed in Table 2 below. Product analysis was done with two gas chromatographs. One was fitted with a packed Carbowax on Carbopak column to determine nitriles in liquids collected in an ice-cooled oxalic acid scrubber. The other was fitted with molecular sieve and is silicone oil columns for analysis of fixed gases and light hydrocarbons in the feed and effluent gas streams. Reaction parameters are summarized in Table 1. The results tests are summarized in Table 2.

TABLE 1

| | Run Conditions | | | Feed Ratios | | | |
| --- | --- | --- | --- | --- | --- | --- | --- |
| | WWH | Temperature | Pressure | $C_3H_8$ | $NH_3$ | $O_2$ | $N_2$ |
| Example 1 | 1.63 | 480° C. | 15 psig | 3 | 0.8 | 2 | 2 |
| Comparative Example A | 1.09 | 480° C. | 15 psig | 3 | 0.8 | 2 | 2 |

TABLE 2

| | Catalyst Density (g/cc) | Propane Conversion (%) | Selectivities (%) | | | | Productivity |
| --- | --- | --- | --- | --- | --- | --- | --- |
| | | | AN | Useful Products | CO | $CO_2$ | |
| Example 1 | 1.0 | 19 | 58 | 75 | 14 | 11 | 0.216 |
| Comparative Example A | 2.4 | 20 | 59 | 76 | 14 | 10 | 0.155 |

Notes:
1. WWH = weight of propane/weight of catalyst/hour.
2. Propane Conversion is defined as the percentage of propane feed which is converted to products or by-products in the reactor.
3. Selectivity is defined as the ratio of moles of acrylonitrile, Useful Products, or carbon monoxides, or carbon dioxide produced to propane converted expressed as a percent.
4. Useful Products = acrylonitrile (AN) + HCN + acetonitrile + acrylic acid + acrolein + propylene.
5. Productivity is defined as the weight in grams of acrylonitrile produced per unit weight in grams of catalyst per hour (g AN/g Catalyst/hr).

The results shown in Table 2 illustrate that the catalyst prepared by the method of the instant invention (Example 1)

has comparable performance to the catalyst made by the prior art method (Comparative Example A) for the ammoxidation of propane. However, the Catalyst of Example 1 has significantly lower density than the catalyst prepared by the prior art method (Comparative Example A). As stated earlier, lower catalyst density means that the catalyst of the invention is more suitable for use in a commercial fluid-bed reactors than higher density catalyst prepared by the prior art methods. The catalyst of the invention (Example 1) also has significantly higher productivity compared to the catalyst made by the prior art method (Comparative Example A).

It is to be understood that the subject invention is not to be limited by the exact description set forth in the examples herein. These have been provided merely to demonstrate the operability of the invention herein described. The selection of catalysts, metal sources, carbon supports, concentrations, contact times, solids loadings, feedstocks, reaction conditions, and products can be determined from the total specification disclosure herein disclosed and described, without departing from the spirit of the invention and the scope of the invention, including modifications and variations, that fall within the boundaries of the attached claims.

That which is claimed is:

1. A process for the preparation of a vanadium antimony oxide catalyst comprising vanadium, antimony, at least one of tin, titanium, iron, chromium and gallium, and optionally at least one element selected from the group consisting of lithium, magnesium, sodium, calcium, strontium, barium, cobalt, nickel, zinc, germanium, niobium, zirconium, molybdenum, tungsten, copper, tellurium, tantalum, selenium, bismuth, cerium, indium, arsenic, boron, aluminum, and manganese, wherein the relative ratios of these elements are represented by the following general formula:

$$V_1Sb_mA_aD_dO_x$$

wherein A is at least one of Ti, Sn, Fe, Cr, and Ga.

D when present is at least one of Li, Mg, Ca, Sr, Ba, Co, Ni, Zn, Ge, Nb,

Zr, Mo, W, Cu, Te, Ta, Se, Bi, Ce, In, As, B, and Mn, m is between about 0.5 to about 10 a is between about 0 to about 10 d is 0 to about 10, and x is determined by the oxidation state of the cations present, wherein the process comprises (i) forming a catalyst precursor slurry comprising a vanadium containing compound and an antimony containing compound in a liquid solvent medium which comprises at least one organic solvent selected from the group consisting of nitriles, carboxylic acids, amines, and sulfides, and (ii) recovering a vanadium antimony oxide from the slurry by drying the slurry in order to remove the liquid solvent medium.

2. The process of claim 1 wherein the liquid solvent medium comprises 10 to 100 wt % organic solvent.

3. The process of claim 1 wherein the liquid solvent medium comprises 50 to 100 wt % organic solvent.

4. The process of claim 1 wherein the liquid solvent medium comprises 80 to 100 wt % organic solvent.

5. The process of claim 1, wherein the catalyst comprises vanadium, antimony, iron, at least one of tin, titanium, chromium and gallium, and at least one other promoter element selected from the group consisting of lithium, magnesium, sodium, calcium, strontium, barium, cobalt, chromium, gallium, nickel, zinc, germanium, zirconium, tantalum, bismuth, cerium, indium, boron, aluminum, and manganese, optionally one or more of molybdenum, tungsten and niobium, and optionally one or more of arsenic, tellurium and selenium, wherein the relative proportions of these elements are represented by the following formula:

$$V_1Sb_bA_cFe_dD_eQ_fR_gO_x$$

where

A is at least one of Ti, Sn, Cr, and Ga

D is at least one of Li, Mg, Ca, Sr, Ba, Co, Ni, Zn, Ge, Zr, Cu, Ta, Bi, Ce, in, B, Al and Mn Q is selected from the group consisting of Mo, W, Nb, R is selected from the group consisting of As, Te, Se, and $0.8 \leq b \leq 4$, $0.01 \leq c \leq 2$, $0.01 \leq d \leq 2$, $0 \leq e \leq 2$, $0 \leq f < 0.01$, $0 \leq g < 0.1$, and x is determined by the oxidation state of the cations present.

* * * * *